United States Patent [19]

Bayless

[11] Patent Number: 5,176,656

[45] Date of Patent: Jan. 5, 1993

[54] AUTOMATICALLY POSITIONED NEEDLE SHEATH FOR A DISPOSABLE HYPODERMIC SYRINGE

[76] Inventor: William B. Bayless, 10132 Beverly Dr., Huntington Beach, Calif. 92646

[21] Appl. No.: 743,698

[22] Filed: Aug. 12, 1991

[51] Int. Cl.⁵ .............................................. A61M 5/32
[52] U.S. Cl. .................................. 604/198; 604/263; 128/919
[58] Field of Search ............... 604/110, 187, 192, 193, 604/194, 195, 197, 198, 263; 128/919

[56] References Cited

U.S. PATENT DOCUMENTS

| | | | |
|---|---|---|---|
| 4,850,977 | 7/1989 | Bayless | 604/198 |
| 4,850,994 | 7/1989 | Zerbst et al. | 604/198 |
| 4,887,998 | 12/1989 | Martin et al. | 604/110 |
| 4,911,693 | 3/1990 | Paris | 604/192 |
| 4,921,490 | 5/1990 | Spier et al. | 604/198 |
| 4,923,447 | 5/1990 | Morgan | 604/198 |
| 4,932,947 | 6/1990 | Cardwell | 604/198 |
| 4,957,490 | 9/1990 | Byrne et al. | 604/197 |
| 4,973,316 | 11/1990 | Dysarz | 604/195 |
| 5,013,305 | 5/1991 | Opie et al. | 604/192 |
| 5,026,353 | 6/1991 | Bartman | 604/192 |

Primary Examiner—C. Fred Rosenbaum
Assistant Examiner—Mark O. Polutta
Attorney, Agent, or Firm—George J. Netter

[57] ABSTRACT

A hypodermic syringe has a barrel, a piston with plunger located in the barrel cavity, an elongated body on the barrel forward end and a needle releasably secured to the body end. A sheath slidingly received onto the elongated body has arms with openings on their end portions which can be locked onto pins on the band exterior. The sheath also has shields which normally extend outwardly. A spring-loaded actuator sleeve is slidingly received on the sheath. When the plunger has emptied the barrel cavity, further movement releases the sheath arms from the pins and the spring-loaded actuator moves over the shields closing about the needle.

11 Claims, 3 Drawing Sheets

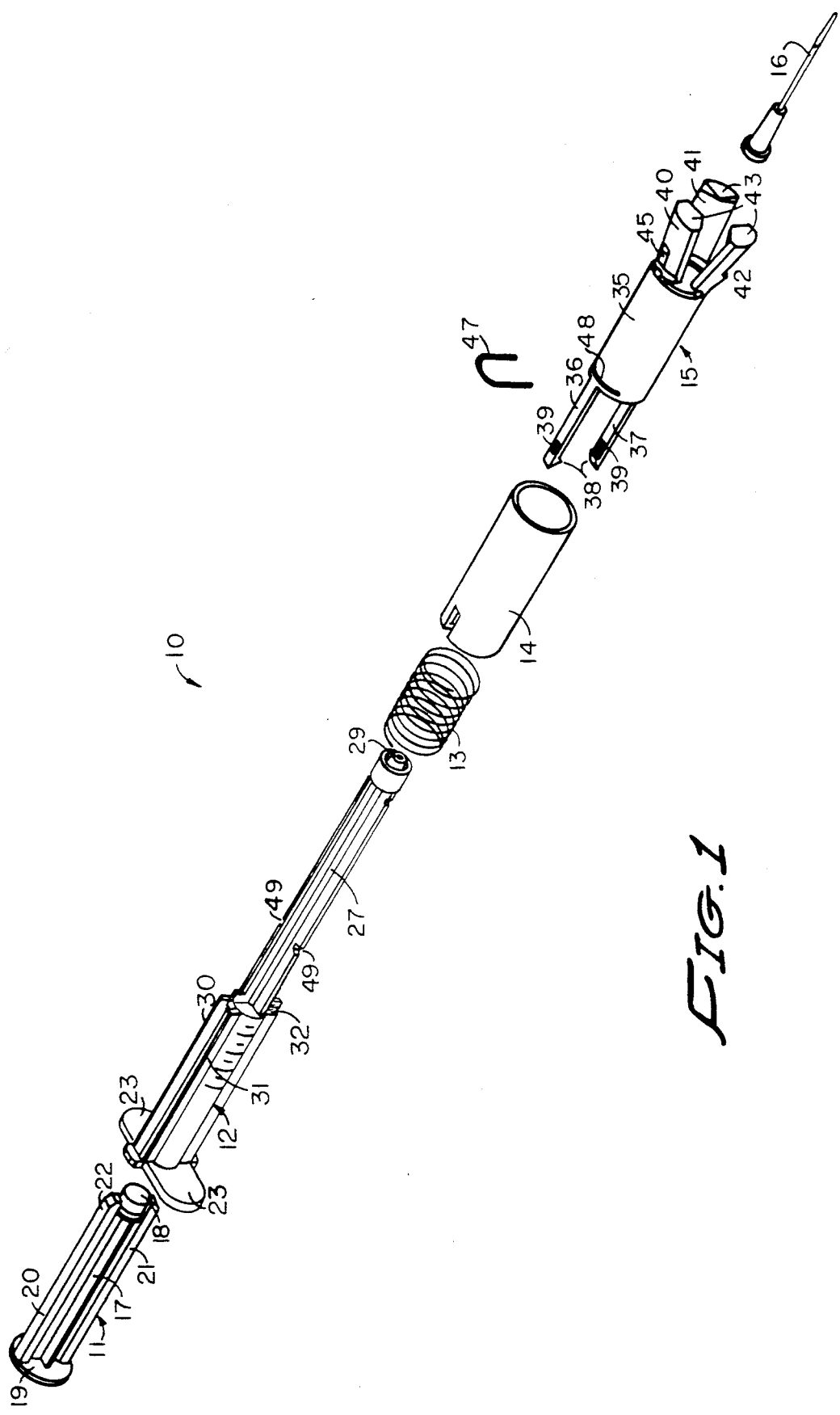

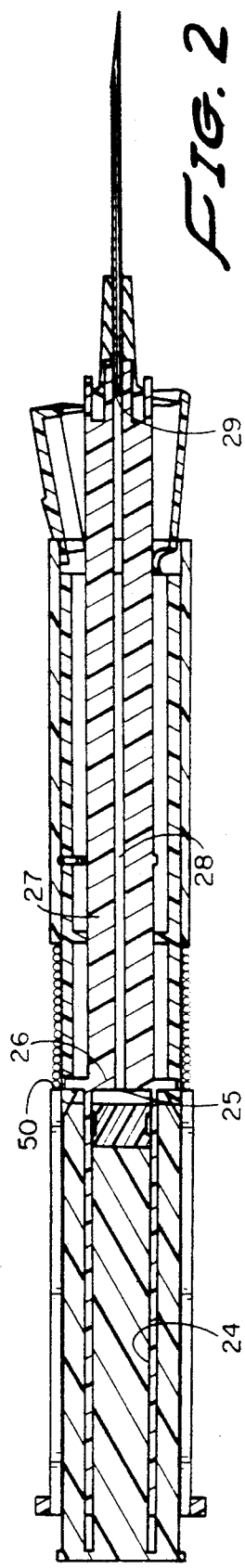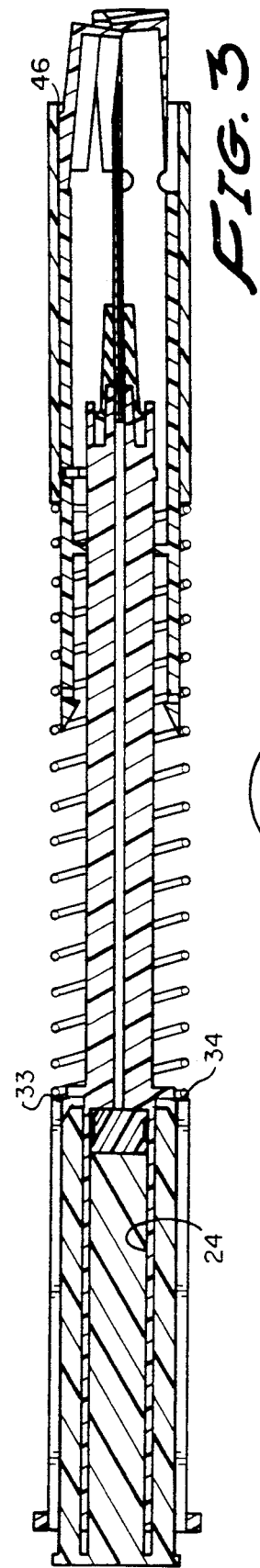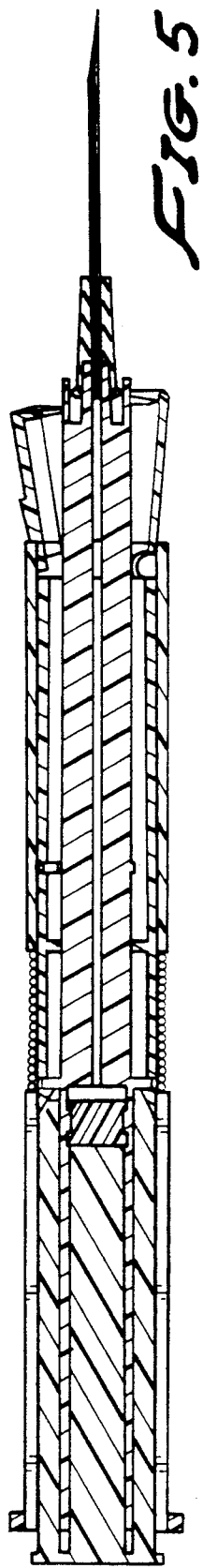

AUTOMATICALLY POSITIONED NEEDLE SHEATH FOR A DISPOSABLE HYPODERMIC SYRINGE

The present invention relates generally to hypodermic needles and syringes, and, more particularly, to a needle sheath construction which automatically encloses the needle at the conclusion of use.

BACKGROUND

Hypodermic needles with syringes have been in extensive use in the medical field for injecting drugs into a patient, and inoculation against disease, for example. There is a continuing problem of injury to doctors, nurses and technicians using such hypodermic devices who become wounded by the needles when they are inadvertently dropped, or accidentally knocked from their hands on movement of the patient. In addition to physical puncture by the needle which, in itself, may be relatively minor, there is the more serious matter of infection with a disease of the patient which can be quite dangerous or even result in death. One very serious disease which can be transmitted in this manner is AIDS.

It is known to reduce needle injury exposure by placing the needles in a puncture resistant container and disposing of the container with included needle. This approach is satisfactory once the needles are in the container; however, it has been found that a substantial percentage of needle injuries result closely adjacent the time of actual use of the needle as a result of being jostled or otherwise dropping the hypodermic needle and syringe inadvertently puncturing the doctor, nurse or technician.

In the past devices have been available which required manually placing a cover over the needle at the conclusion of its use. However, these devices could not readily be operated with one hand, and, in fact, if this were tried there would be an increased possibility of injury occurring.

U.S. Pat. No. 4,850,977, BUTTON ACTIVATED AUTOMATIC NEEDLE SHEATH FOR DISPOSABLE SYRINGE, by the same inventor as the present application, discloses a sheath which can be moved into covering and uncovering relation to the needle by finger actuation of a lever arm located on the outside surface of the hypodermic syringe. Although the device can be operated with one hand alone, the hand must be shifted around a certain extent to effect actuation and the hypodermic device can be dropped at this time possibly resulting in injury.

In a further U.S. Pat. No. 4,863,434, AUTOMATIC NEEDLE SHEATH FOR DISPOSABLE SYRINGE, by this same inventor a movable protective sheath for a hypodermic syringe has a ball-like member received within an expandable undersize opening for holding the sheath in the needle-exposed relation. On pressing the plunger a slight amount farther after emptying the hypodermic barrel, the ball-like member is forced from a locking opening and a coil spring drives the sheath into needle-covering position. This device can be operated with one hand, also.

OBJECTS AND SUMMARY OF THE DISCLOSURE

It is a primary aim and object of the present invention to provide an improved hypodermic needle and syringe of the disposable kind which includes a sheath that moves into covering relationship to the needle automatically upon completion of fluid dispensing while holding the device in one hand alone and without unusual manipulation that might result in dropping the device.

In accordance with the present invention there is provided a hypodermic syringe construction having a hollow syringe chamber within which material to be dispensed is located and having means for gripping with the first and second fingers adjacent one end. A piston having an outer thumb pressure actuator is located within the cylinder chamber. The lower end of the syringe chamber of barrel interconnects with a barrel extension member having an internal passageway connected to the syringe barrel. The needle is releasably received upon the outer end of the extension member in conventional manner.

A cylindrical open-ended protective sheath has a plurality of movable shields located adjacent one end and resiliently extending radially outwardly of the sheath main body. At the opposite end of the sheath are a pair of elongated arms extending longitudinally from the cylindrical body and having beveled ends, each arm having an opening extending transversely therethrough.

A cylindrical actuator has a bore enabling sliding receipt over the sheath for moving the movable shields of the sheath about the needle after use. The sheath and actuator are slidingly received upon the barrel extension member and spring-loaded thereon to be resiliently urged away from the syringe barrel.

In the needle exposed mode, the sheath and actuator are at one extreme on the syringe extension member compressing the spring and the sheath arms have the openings in their end portions located on upstanding pins on the syringe barrel lockingly holding the parts in that position. At this time, the movable shields are extended outwardly allowing the needle to be exposed for use.

Assuming a quantity of fluid containing medicaments or the like is in the syringe barrel, the piston can then be driven forwardly by placing the thumb on the outer end of the thumb pressure actuator and gripping the cylinder with the index and third finger. When substantially the total amount of fluid has been dispensed and the piston is almost at the bottom of the syringe barrel, a cam portion on the piston drives against the beveled ends of the sheath arms moving them out of their locked position on the pins. When this happens, the spring now drives the sheath and the actuator sleeve forwardly over the movable shields and in that way forms a protective wall about the needle. The sheath is now in its locked and protective covering relation about the needle permitting disposal or other handling of the hypodermic syringe without fear of injury to anyone. The sheath can only be removed by affirmatively gripping the sleeve, pulling it back toward the syringe which simultaneously pulls the sheath toward the syringe, and at the end of this motion locates the sheath arms opening onto the locking flange pins.

The entire operation of using the hypodermic syringe in its accustomed use, including administering a dosage of a medicament and locking the needle into a protective covering relationship when completed, can be easily accomplished solely while holding the syringe in one hand.

DESCRIPTION OF THE DRAWING

FIG. 1 is a perspective exploded view of a hypodermic syringe with protective sheath parts of the present invention;

FIG. 2 is a side elevational, sectional view of a hypodermic syringe with sheath protection shown with needle exposed for use;

FIG. 3 is a side elevational, sectional view similar to FIG. 2 showing the sheath in protective covering relation about the needle;

FIG. 4 is an end elevational view taken along the line 4—4 of FIG. 3;

FIG. 5 is a side elevational, sectional view similar to FIGS. 2 and 3 showing an interim position immediately after (or before) the sheath is locked open.

DESCRIPTION OF PREFERRED EMBODIMENTS

Figure 6:
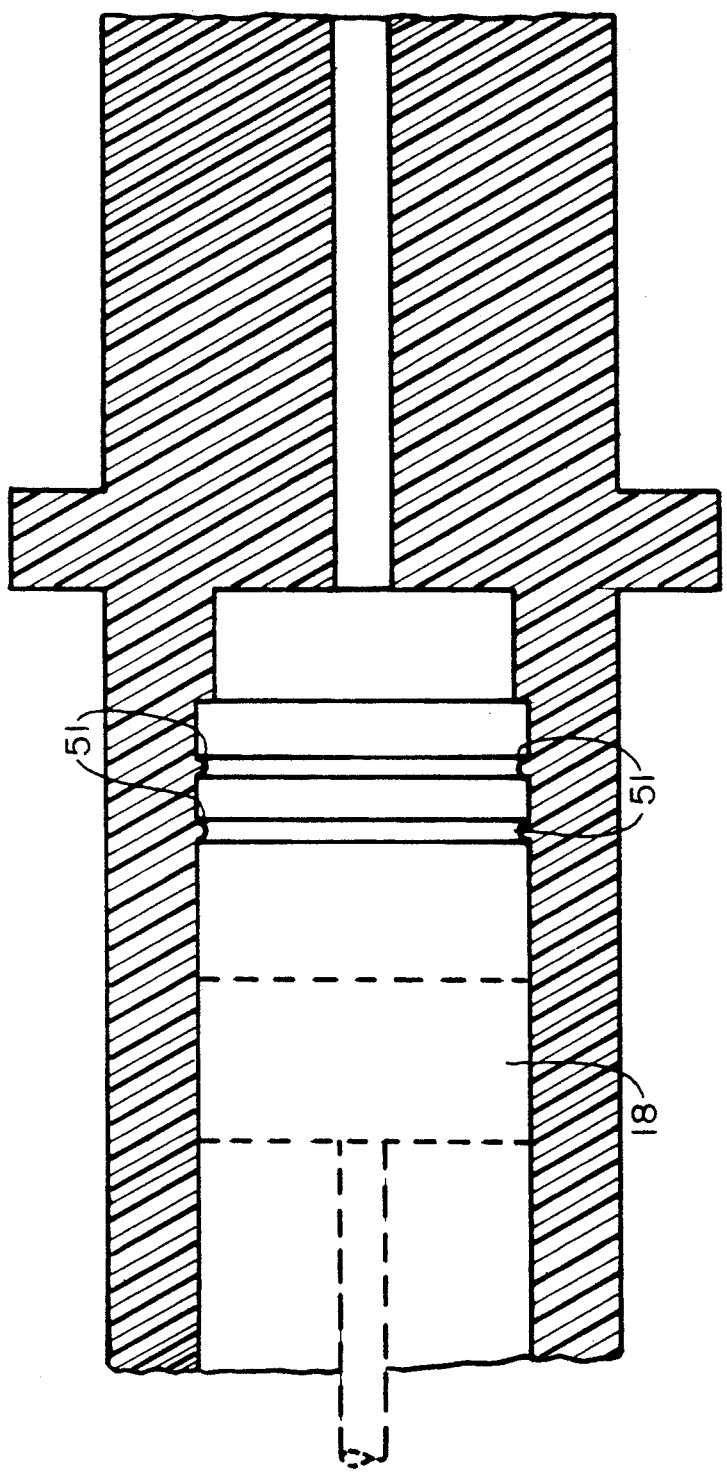
FIG. 6 is a sectional, partially fragmentary, enlarged view of the syringe barrel.

Accidental injury and infection to doctors, nurses and technicians from hypodermic needles has been on the rise in recent years. The injury frequently occurs when the one administering a shot to a patient is jostled, bumped into, or otherwise inadvertently drops the hypodermic syringe and is punctured or lacerated by the needle. The resulting injury can be severe and painful of itself, however the primary concern is infection. Of special present concern is the possibility of infection with diseases such as infectious hepatitis or AIDS, for example, which is readily transmitted by a hypodermic needle.

Accordingly, it is highly desirable to have a hypodermic syringe with a protective means covering the needle which acts automatically on completion of normal use and which can be operated solely with one hand without requiring dexterous manipulation. This one-handed use feature is especially important in dealing with a patient where there is always the possibility that the patient will move or jostle the one giving a shot causing that individual to drop the syringe and accidentally be punctured or lacerated by the needle.

Turning now to the drawing and with particular reference to FIG. 1, the hypodermic needle syringe with protective sheath is enumerated generally as 10. As shown in exploded relation there, the device includes in its major parts a piston 11, a syringe barrel 12 enclosing a chamber within which liquid medicaments are located, a drive spring 13, a sleeve actuator 14, a needle sheath 15 and the needle 16.

The piston 11 has an elongated body 17 terminating at one end in a plunger 18 of such dimensions as to enable sliding receipt within the syringe barrel 12 for pressurized dispensing of fluids contained therein. The opposite (outside) end of the piston includes a pressure plate 19 against which the thumb typically applies force in use of the device. The piston body also has a pair of elongated guides 20 and 21 arranged in parallel spaced relation to the body, each being cantilever mounted to the pressure plate 19. The outer ends of 20 and 21 are tapered inwardly at 22 to form a camming surface for a use to be described.

The syringe barrel 12 has first and second ears or tabs 23 at one end extending transversely of the body portion typically for gripping by the index and third fingers. A generally cylindrical cavity 24 extends from an open end adjacent the tabs 23 inwardly terminating at a reduced diameter opening 25 in an outer end wall 26 (FIG. 2). Cross-sectional dimensions of the cavity are such as to slidingly receive the piston plunger 18 therewithin while also sealing against fluid passage between the plunger and barrel walls.

A barrel extension member 27 has an elongated body extending axially from the end wall 26 within which a passageway 28 communicates the cavity 24 to the exterior via end opening 29. A first pair of upstanding guide walls 30 and 31 on the outer surface of the barrel 12 extend generally parallel to the barrel longitudinal axis. These guide walls are spaced apart sufficiently to enable sliding receipt of guide 20 or 21 serving to confine the guide movement against rotation during operation of the syringe. A second set of guide walls 32 (only one is shown) which can be identical to 30 and 31, are located on the opposite side of the barrel and are dimensioned to receive the other guide 21 in the same manner as the guide 20. In this way, the two sets of guide walls track the piston movement of the piston along the barrel body and prevent relative rotation. The end wall 26 extends radially outwardly a slight amount to form locking pins 33 and 34 for a purpose to be described later.

The protective needle sheath 15 consists of a hollow tubular body 35 open at both ends and having at one end first and second arms 36 and 37, respectively, extending parallel to the tubular body axis and each terminating in a tapered or beveled end portion 38. More particularly, the two arms are located at 180 degrees from each other with the tapered portions facing each other, i.e., toward the axis of the shield. Spaced slightly rearwardly of each tapered end 38 is a transversely extending opening 39 which passes completely through the arm body and which has a use to be described. Although other shapes may be found to work satisfactorily, preferably the opening cross-section is rectangular. At the opposite end of the sheath body 35, three movable shields 40, 41 and 42, arranged at 120 degrees angular spacing about the body longitudinal axis, are resiliently and hingedly connected to the body 35 so as to extend both longitudinally and slightly radially outward. Each shield terminates at its outermost end in a substantially triangular tab 4 extending inwardly toward the axis of body 35.

Each movable shield interconnects with the end of the sheath body 35 via a separate resilient means 44 such as a unitary piece of resilient plastic having springlike characteristics to cant the movable shields radially outwardly from the body while resiliently permitting them to be forced radially inward as will be described.

The sleeve actuator 14 is essentially an open-ended cylindrical tube having an internal bore of such dimensions as to permit close sliding receipt over the sheath body 35 and upon being received still farther thereon to force the movable shields 40-42 radially inward so that their outer surfaces conform to that of the sheath body. In this latter condition the tabs 43 are brought into close slightly overlapping relationship to form a single generally imperforate end wall (FIGS. 3 and 4).

Moreover, a notch 45 on the outside surface of each of the movable shields is lockingly engageable with an inwardly directed flange 46 on an inner end portion of the sleeve actuator when the actuator is extended over the shields as shown in FIG. 3.

When the hypodermic syringe is assembled, the sheath 15 is received within the sleeve actuator, and the drive spring 13 is located on the barrel extension member 27 in pressure exerting relation to the end of actuator 14. A U-shaped metal clip 47 is inserted through a slot 48 in sheath body 35 and has portions lockingly positioned within notches 49 on extension member 27. The needle 16 may be mounted at this time onto the end of the extension member.

In typical operation for administering a medicament located in the barrel cavity 24, the sleeve actuator is moved along the extension member toward the syringe barrel 12 which causes the sheath arms 36 and 37 to move between the upstanding walls 30-32 and have the openings 39 locked onto 50 at the end of the barrel as shown in FIG. 2.

When the piston is pushed during an injection, the side members 21, 22 move down the guideway formed by 31, 32 until the stroke is completed. The ramps on 21, 22 lift the opposing ramps 38 of the sheath extension arms 36, 37 allowing the spring to push the collar 14 and the sheath 15 forward. Both collar 14 and sheath 15 move together until 15 is stopped by the retainer 47 dropping into the notch 50 of the syringe extension 27. At that point the ends 43 of the sheath 15 move radially inward as they pass over the end of the needle and as the collar 14 drives over the ramps and is then stopped by the rear of the sheath 15 at the base of the extension arms 36, 37.

FIG. 6 shows an enlarged sectional view of the barrel cavity 24 adjacent the end wall 26. There are several ribs or protrusions 52 on the inner wall which can be tactilely sensed as the plunger 18 moves across them to inform the user that the normal injection stroke is complete. When these are felt the plunger is then forced still farther and past the ribs to release the protective sheath which is accomplished by the bevel 22 on the guides 20 and 21 camming the tapered end portions 38 of the arms 36 and 37 radially outwardly releasing the arms openings 39 from the pins 33, 34. With the pins no longer locking with the arms, the spring can drive the sheath into covering relation to the needle.

What is claimed is:

1. A hypodermic syringe including apparatus for enclosing the needle of the hypodermic syringe to prevent inadvertent injury therefrom, comprising:
   a syringe barrel housing having a cavity, a first opening at one end and an opposite end having second opening smaller than said first opening, said housing including pin means on an external surface thereof;
   an elongated body secured to the barrel housing, said body including an internal passageway extending completely through the body which is in communication with the barrel housing second opening and an end of the body adapted for receiving the hypodermic needle thereon;
   a hollow generally tubular sheath means slidingly received on the elongated body including,
   arm means extending inwardly from the sheath means generally parallel to the barrel housing and having a transverse opening therein for receiving the barrel housing pin means therein, and a plurality of movable shields resiliently and hingedly connected to the sheath means said shields in the relaxed unstressed state extending angularly laterally outwardly from the tubular sheath means;
   piston means having a plunger received within the barrel housing first opening for sliding movement along the cavity including a guide means for engaging the arm means;
   a sleeve actuator slidingly received onto the sheath means and movable from a first position forcing the movable shields laterally toward one another to enclose the needle and to a second position releasing the movable shields to the relaxed state extending laterally outwardly from the tubular sheath of means leaving the needle exposed; and
   spring means engaging the sleeve actuator and resiliently urging said actuator away from the barrel housing to the actuator first position enclosing the needle with the shield means when the pin means is removed from the arm means transverse opening by the guide means.

2. A hypodermic syringe as in claim 1, in which the arm means includes first and second arms unitary with said sheath means and located on opposite sides of said sheath means, said first and second arms each having an inwardly tapering end portion.

3. A hypodermic syringe as in claim 2, in which the pin means includes first and second pins secured to the barrel housing outer surface on opposite sides thereof and adjacent to the elongated body.

4. A hypodermic syringe as in claim 1, in which the movable shields are connected to the tubular sheath means by an integrally related spring-like plastic material which resiliently urges the shields outwardly away from the tubular sheath.

5. A hypodermic syringe as in claim 1, in which the movable shields each include a side portion and an end tab extending transversely of the side portion, the tabs overlapping with each other when the sleeve actuator is in its first position.

6. A hypodermic syringe as in claim 1, in which the actuator sleeve includes an inwardly directed flange that engages with notches on the outer surface of the movable shields when the sleeve actuator is in its first position.

7. A hypodermic syringe as in claim 1, in which the spring means includes a coil spring received one the elongated body with one end contacting the barrel housing and the other end engaging the actuator sleeve.

8. A hypodermic syringe as in claim 1, in which the piston means includes guide means extending along the outer surface of the barrel housing, said guide means having beveled end portions which engage the arm means ends and cam them off the pin means.

9. A hypodermic syringe as in claim 8, in which the guide means are located between guide walls on the outer surface of the barrel housing.

10. A hypodermic syringe as in claim 9, in which the guide means include two guides located on opposite sides of the piston means, respectively, and two pairs of guide walls, one pair for each guide.

11. A hypodermic syringe as in claim 1, in which the barrel housing cavity wall has inwardly directed protrusions which can be tactilely sensed on the plunger moving therepast advising the user of the syringe that further movement of the piston means will move the sheath means into protective covering relation of the needle.

* * * * *